United States Patent [19]
Hubert et al.

[11] Patent Number: 5,138,646
[45] Date of Patent: Aug. 11, 1992

[54] X-RAY DIAGNOSTICS APPARATUS FOR A BEDRIDDEN PATIENT

[75] Inventors: Guenter Hubert, Baiersdorf; Gerhard Seyler, Bubenreuth; Gerd Wessels, Erlangen, all of Fed. Rep. of Germany

[73] Assignee: Siemens Aktiengesellschaft, Munich, Fed. Rep. of Germany

[21] Appl. No.: 461,321

[22] Filed: Jan. 5, 1990

[30] Foreign Application Priority Data

Feb. 10, 1989 [EP] European Pat. Off. ........ 89102329.3

[51] Int. Cl.⁵ ............................................. G03B 42/02
[52] U.S. Cl. ................................. 378/177; 378/181; 378/182; 378/198
[58] Field of Search ............... 378/177, 178, 179, 198, 378/181, 182, 187, 195, 198, 208, 209, 20, 37, 108, 110, 206, 205, 170; 334/8, 9; 5/65, 63; 340/825.72; 341/176

[56] References Cited

U.S. PATENT DOCUMENTS

| | | | |
|---|---|---|---|
| 2,873,456 | 2/1959 | Joy | 5/65 |
| 3,671,745 | 6/1972 | Fouquart | 378/179 |
| 3,883,736 | 5/1975 | Liddell | 334/8 |
| 3,959,832 | 6/1976 | Parsons | 5/65 |
| 4,082,953 | 4/1978 | Krause et al. | 378/97 |
| 4,092,544 | 5/1978 | Grim | 378/206 |
| 4,193,148 | 3/1980 | Rush | 378/177 |
| 4,651,364 | 3/1987 | Hayton et al. | 378/179 |
| 4,843,665 | 7/1989 | Cockel et al. | 5/65 |
| 5,016,268 | 5/1991 | Lotman | 378/177 |

FOREIGN PATENT DOCUMENTS

| | | | |
|---|---|---|---|
| 774254 | 9/1934 | France | 5/65 |
| 856797 | 12/1960 | United Kingdom . | |
| 1200814 | 8/1970 | United Kingdom . | |

Primary Examiner—Janice A. Howell
Assistant Examiner—Don Wong
Attorney, Agent, or Firm—Hill, Van Santen, Steadman & Simpson

[57] ABSTRACT

An x-ray diagnostics apparatus for obtaining an x-ray exposure of a bedridden patient permits the exposure to be obtained without moving the patient from the bed. The patient bed has two patient bearing surfaces. The patient lies on the upper surface, and a lower surface is vertically adjustable beneath the upper surface. When the lower surface is lowered to permit the introduction of an x-ray cassette between the upper and lower surfaces, the upper surface is supported, such as by a fabric tentered to the bed frame. An optical system is provided for accurately positioning the x-ray film cassette, and a wireless transmission path for an automatic exposure unit may also be provided.

7 Claims, 3 Drawing Sheets

X-RAY DIAGNOSTICS APPARATUS FOR A BEDRIDDEN PATIENT

BACKGROUND OF THE INVENTION

1. Field of the Invention

The present invention is directed to an x-ray diagnostics apparatus, and in particular to such an apparatus which includes a patient bed and which permits x-ray exposures to be obtained without removing the patient from the bed.

2. Description of the Prior Art

It is frequently necessary to obtain x-ray exposures of bedridden patients, for example, in an intensive care station. It is known for this purpose to arrange the x-ray source on a portable stand which can be brought to the patient's bed for generating the x-ray exposures. In these known devices, however, the patient must be lifted by attendants so that the x-ray film cassette can be inserted between the patient and the supporting surface of the patient's bed. The x-ray source is then positioned above the patient's bed.

The necessity of lifting the patient to produce an x-ray disclosure is undesirable, and moreover precise centering and gating of the x-ray source constitutes a problem in these known devices.

SUMMARY OF THE INVENTION

It is an object of the present invention to provide an x-ray diagnostics apparatus which permits x-ray exposures to be obtained of a bedridden patient without the necessity of lifting the patient from the bed to produce the x-ray exposure.

It is a further object of the present invention to provide such an x-ray diagnostics apparatus wherein a simple and precise centering of the x-radiation from the x-ray source relative to the x-ray film cassette is possible.

These objects are achieved in accordance with the principles of the present invention in an x-ray diagnostics apparatus wherein the patient bed has two bearing surfaces, with the patient being directly supported on an upper bearing surface, and the lower bearing surface being vertically adjustable so that an x-ray film cassette can be inserted between the two bearing surfaces. The lower bearing surface can be lowered when a patient is lying on the upper bearing surface, and an x-ray film cassette, preferably contained in a cassette holder attached to a carriage which can be moved to the patient's bed, can easily be inserted.

The x-ray diagnostics apparatus also includes an alignment system with which the x-ray film cassette can be precisely positioned relative to the x-radiation from the x-ray source.

DESCRIPTION OF THE PREFERRED EMBODIMENTS

Figure 1:
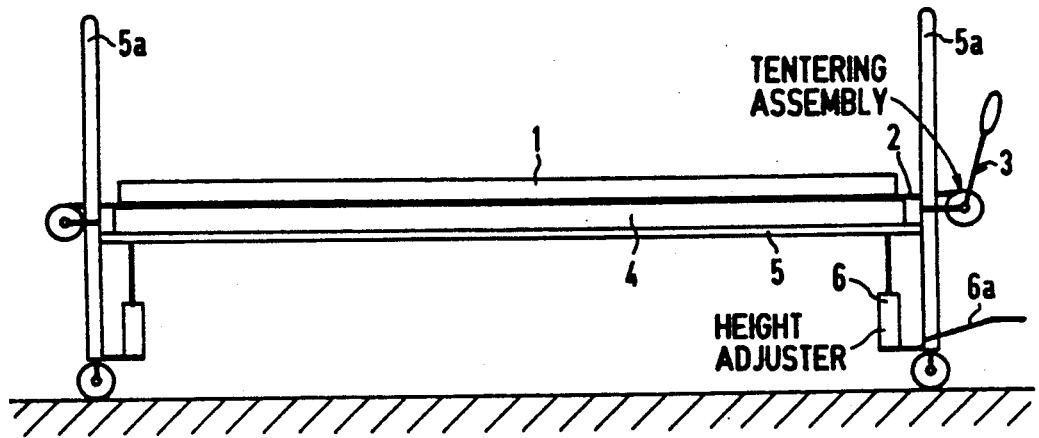
FIG. 1 is a side view of a patient bed used in an x-ray diagnostics apparatus constructed in accordance with the principles of the present invention, showing the two bearing surfaces disposed next to each other for normal patient usage.
Figure 2:
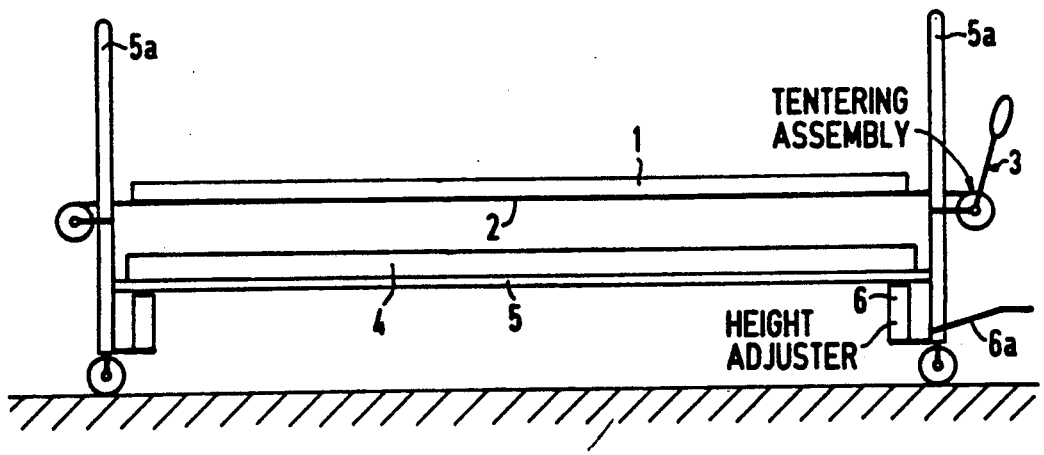
FIG. 2 is a side view of the patient bed of FIG. 1 showing the bearing surfaces separated for use in obtaining an x-ray exposure.

FIGS. 1 and 2 shows respective side views of a patient bed for use in an x-ray diagnostics apparatus constructed in accordance with the principles of the present invention. The bed comprises a mat 1 of expanded (foam) material. The mat 1 is, in normal usage, supported on top of a mattress 4, which is in turn supported by a horizontal support 5 attached to vertical frame elements 5a. A fabric 2 is disposed between the mat 1 and the mattress 4, and is able to be rendered taut by a tentering assembly 3, attached to one of the vertical frame elements 5a. The vertical position of the horizontal support 5 and the mattress 4 can be adjusted hydraulically by a vertical adjustment element 6, which includes a lever 6a.

The mat 1 consisting of foam material and the fabric 2 are transmissive for x-rays. A patient normally lies on the mat 1 of the bed with the bed in the form shown in FIG. 1. When an x-ray exposure is to be taken, the fabric 2 is tensed by the tentering assembly 3, such as by operating the lever shown in the drawings. Subsequently, the mattress 4 and the horizontal support 5 are lowered to the position shown in FIG. 2. An x-ray film cassette can then be inserted in the free space between the fabric 2 and the mattress 4. The patient need not be moved during this entire sequence. After the x-ray exposure is completed, the mattress 4 and the horizontal support 5 are moved upwardly by the vertical adjustment 6, and the fabric 2 is relaxed by again operating the tentering assembly 3. The patient is then again fully supported by the mattress 4 and the horizontal support 5.

Instead of hydraulically adjusting the vertical position of the mattress 4 and the horizontal support 5, it is also possible to use other known vertical adjustment means, for example, an articulated lever mechanism or an electric motor.

Figure 3:
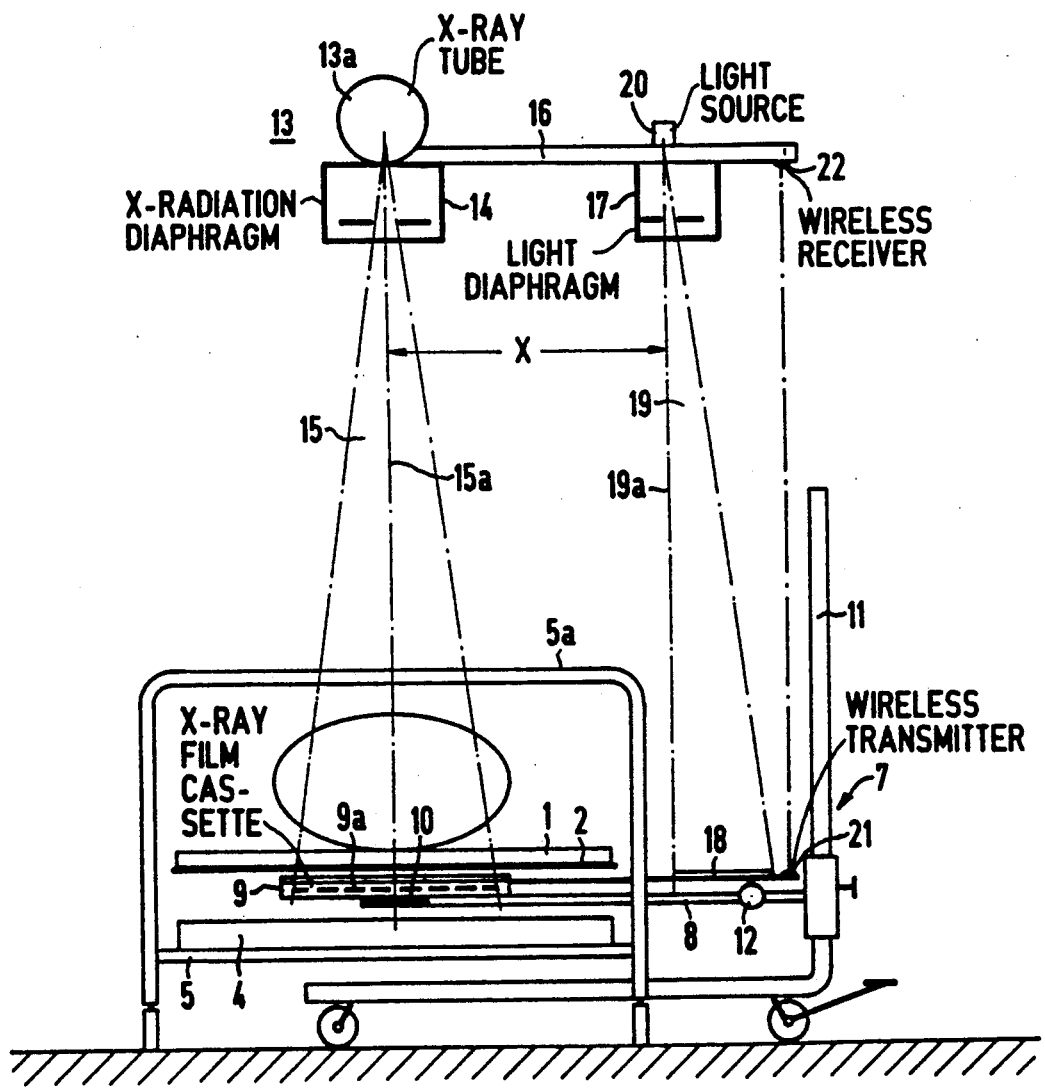
FIG. 3 is an end view of the patient bed in the position shown in FIG. 2, with remainder of the x-ray diagnostics apparatus constructed in accordance with the principles of the present invention also being present.

An end view of the patient bed, in the position shown in FIG. 2, is shown in FIG. 3 together with the other components of the x-ray diagnostics apparatus. These include a carriage 7 which carries a cassette holder 8, the cassette holder 8 having a cassette compartment 9 for and x-ray film cassette 9a. An x-radiation detector 10 is disposed behind the cassette compartment 9 in the diretion of radiation propagation. The cassette holder 8 is adjustable in height by means of a stand 11 of the carriage 7, and is mounted so as to be pivotable around a horizontal axis 12. The x-ray film cassette 9a is introduced between the fabric 2 and the mattress 4 at the proper height, in the manner explained above.

The x-ray diagnostics installation also includes an x-radiator assembly 13. The x-radiator assembly 13 may be supported relative to the patient in any known manner, the details of which are not shown in the drawings. The x-radiator assembly 13 includes an x-ray source 13a which generates an x-ray beam 15 with the assistance of a primary radiation diaphragm 14. The x-ray beam 15 has a central ray 15a.

For aligning the x-ray film cassette 9a with reference to the x-ray beam 15, a radiation diaphragm 17 is provided which produces an optical graticule in an adjustment field 18 of the cassette holder 8. The radiation diaphragm 17 is mounted on an arm or boom 16 of the x-radiator assembly 13. The adjustment field 18 is at a lateral distance from the cassette compartment 9 so that the optical radiation proceeds laterally past the patient bed. A marking or markings applied in the adjustment field 18 are brought into coincidence with the graticule. The x-ray film cassette 9a in the cassette compartment 9 is then aligned to the exposure field. For this purpose, the radiation diaphragm 17 is adjusted in a synchronized manner with the primary radiation diaphragm 14. The radiation used for this alignment may be a light beam 19 generated by a light source 20. The light beam 19 has a vertically proceeding light ray 19a.

The distance X of the radiation diaphragm 17 from the primary radiation diaphragm 14 is taken as the distance of the vertical light beam 19a from the central ray 15a of the x-ray beam 15, which is parallel thereto. The radiation diaphragm 17 forms half of a further graticule, and the exposure field on the patient can be illuminated through the primary radiation diaphragm 14, with a light beam localizer having a complete optical graticule. With the half graticule and half of the cassette size in the adjustment field 18, the cassette carriage 7 can be aligned precisely parallel to the patient bed and perpendicular to the central ray 15a. The desired cassette size can be precisely gated in the cassette plane. Only half of the cassette size is reproduced within the adjustment field 18.

The carriage 17 is locked after the adjustment. The cassette holder 8 can be easily interchanged with other cassette sizes having associated scattered ray grids.

The radiation dose measurement is undertaken via the x-ray detector 10, which supplies and electrical signal which is wirelessly transmitted by an infrared transmitter 21, and is received by a receiver 22 mounted at the arm 16 of the x-radiator assembly 13, for controlling an automatic exposure unit 23. The high voltage supply (not shown) for the x-ray source 13a can be in the form of a rechargeable unit, which can be recharged at a receptacle when the apparatus is not in use.

Figure 4:
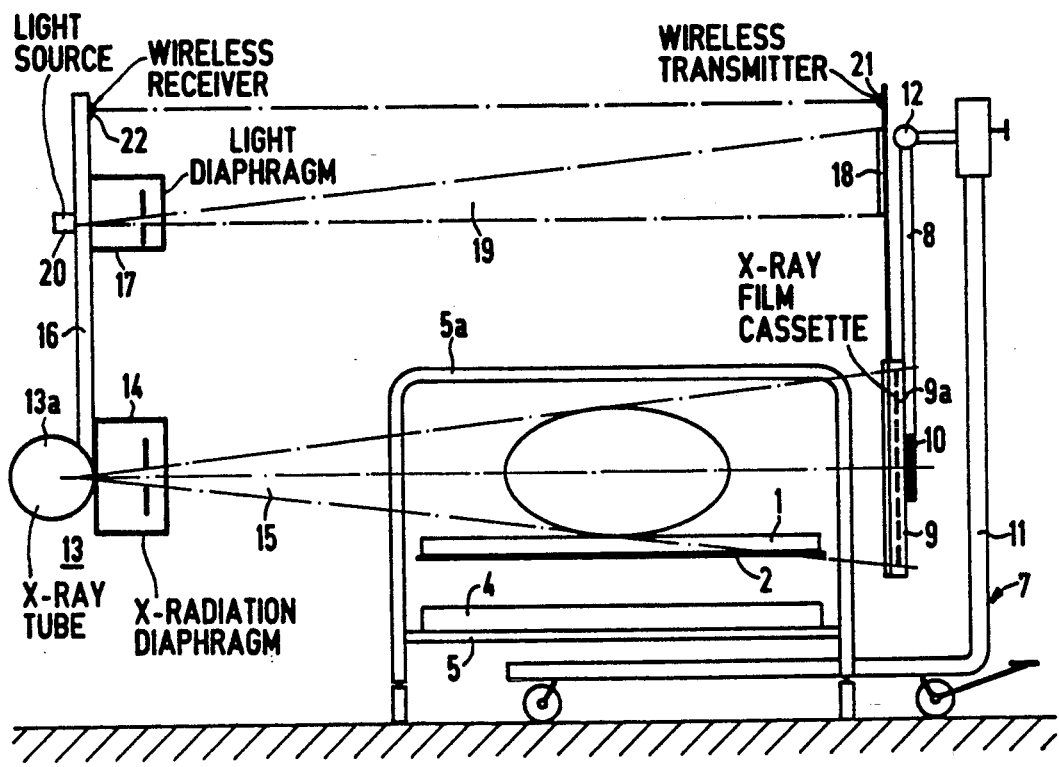
FIG. 4 is a further end view of x-ray diagnostics installation constructed in accordance with the principles of the present invention with the x-ray generating and exposure units being positioned for obtaining a lateral exposure.

The cassette holder 8 is shown in FIG. 4 pivoted by 90° around the axis 12, so that a transverse exposure can be made. The centering and gating are undertaken in the same manner as described above for a vertical exposure.

As can be seen from FIGS. 3 and 4, the carriage 7 is adjustable completely independently of the x-radiator assembly 13. A simple and reliable alignment of the cassette 9a in the cassette compartment 9 relative to the x-ray beam 15 is nonetheless assured. The arm or boom 16 of the x-radiator assembly 13 can be secured to a separate portable carriage, or to a three-dimensionally adjustable sealing support.

Although further modifications and changes may be suggested by those skilled in the art, it is the intention of the inventors to embody within the patent warranted hereon all changes and modifications as reasonably and properly come within the scope of their contribution to the art.

We claim as our Invention:

1. An x-ray diagnostics apparatus for obtaining an x-ray exposure of a bedridden patient comprising:
   a patient bed having first and second bearing surfaces, said first bearing surface adapted to support a patient thereon, and said second bearing surface being disposed below said first bearing surface;
   means for generating an x-ray image of said patient including means for generating an x-ray beam in which said patient is disposed and an x-ray film cassette on which x-rays attenuated by said patient are incident to form said image; and
   said bed further having means for vertically adjusting the position of said second bearing surface so that said second bearing surface normally supports said first bearing surface and is lowerable away from said first bearing surface to permit the introduction of said x-ray film cassette between said first and second bearing surfaces to obtain said x-ray image.

2. The x-ray diagnostic apparatus of claim 1, wherein said means for generating an x-ray image includes means for pivotally mounting a cassette holder so that a vertical or horizontal x-ray exposure can be made.

3. The x-ray diagnostic apparatus of claim 1, further comprising:
   a light transmitter disposed at a fixed position relative to said x-ray beam, said light transmitter generating a light beam which is incident on an adjustment field of a cassette holder.

4. The x-ray diagnostic apparatus of claim 1, further comprising:
   means for measuring the radiation dose supplied to a patient; and
   means for wirelessly transmitting information identifying said radiation dose to an x-ray source, and means for controlling the radiation dose based on the received information.

5. The x-ray diagnostic apparatus of claim 4, wherein said x-ray source is mounted on an arm, and wherein a transmitter for said information is disposed on x-ray cassette holder and a receiver for said information is mounted on said arm.

6. An x-ray diagnostic apparatus for obtaining an x-ray exposure of a bedridden patient comprising:
   a patient bed having first and second bearing surfaces, said first bearing surface adapted to support a patient thereon, and said second bearing surface being disposed below said first bearing surface;
   means for generating an x-ray image of said patient including means for generating an x-ray beam in which said patient is disposed and an x-ray film cassette on which x-ray attenuated by said patient are incident to form said image;
   a fabric disposed between said first and second bearing surfaces;
   means for tentering said fabric to support said first bearing surface when said second bearing surface is lowered; and
   said bed further having means for vertically adjusting the position of said second bearing surface so that said second bearing surface normally supports said first bearing surface and is lowerable away from said first bearing surface to permit the introduction of said x-ray film cassette between said first and second bearing surfaces to obtain said x-ray image.

7. An x-ray diagnostic apparatus for obtaining an x-ray exposure of a bedridden patient comprising:
   a patient bed having first and second bearing surfaces, said first bearing surface adapted to support a patient thereon, and said second bearing surface being disposed below said first bearing surface;
   means for generating an x-ray image of said patient including means for generating an x-ray beam in which said patient is disposed and an x-ray film cassette on which x-ray attenuated by said patient are incident to form said image;

means for selectively supporting said first bearing surface, disposed between said first and second bearing surfaces, said means for selectively supporting said first bearing surface being employed to support said first bearing surface only when said second bearing surface is lowered away from said first bearing surface; and said bed further having means for vertically adjusting the position of said second bearing surface so that said second bearing surface normally supports said first bearing surface and is lowerable away from said first bearing surface to permit the introduction of said x-ray film cassette between said first and second bearing surfaces to obtain said x-ray image.

* * * * *